(12) United States Patent
Yamazaki et al.

(10) Patent No.: US 9,887,063 B2
(45) Date of Patent: Feb. 6, 2018

(54) RADIATION GENERATING TUBE, RADIATION GENERATING APPARATUS, RADIOGRAPHY SYSTEM AND MANUFACTURING METHOD THEREOF

(71) Applicant: CANON KABUSHIKI KAISHA, Tokyo (JP)

(72) Inventors: Koji Yamazaki, Ayase (JP); Yasue Sato, Machida (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 113 days.

(21) Appl. No.: 14/356,578

(22) PCT Filed: Oct. 25, 2012

(86) PCT No.: PCT/JP2012/006845
§ 371 (c)(1),
(2) Date: May 6, 2014

(87) PCT Pub. No.: WO2013/069222
PCT Pub. Date: May 16, 2013

(65) Prior Publication Data
US 2014/0369467 A1    Dec. 18, 2014

(30) Foreign Application Priority Data

Nov. 9, 2011  (JP) .................................. 2011-245793

(51) Int. Cl.
*H01J 35/00*    (2006.01)
*H01J 35/16*    (2006.01)
(Continued)

(52) U.S. Cl.
CPC .............. *H01J 35/16* (2013.01); *G01N 23/02* (2013.01); *H01J 5/26* (2013.01); *H01J 9/26* (2013.01);
(Continued)

(58) Field of Classification Search
CPC .... H01J 2209/18; H01J 2209/26; H01J 35/16; H01J 5/26; H01J 9/26; H01J 9/32; H01J 9/36; H01J 35/26
See application file for complete search history.

(56) References Cited

U.S. PATENT DOCUMENTS 3,553,514 A    1/1971  Berends
6,015,325 A *  1/2000  Inazuru ................. H01J 35/165
                                                      228/187

(Continued)

FOREIGN PATENT DOCUMENTS

JP    H03-156846 A    7/1991
JP    07-296754 A     11/1995
(Continued)

*Primary Examiner* — Dani Fox
(74) *Attorney, Agent, or Firm* — Canon U.S.A., Inc. IP Division

(57) ABSTRACT

The present invention relates to a radiation generating tube. The radiation generating tube includes an envelope including an insulating tubular member having at least two openings, a cathode connected to one of the openings of the insulating tubular member, and an anode connected to the other of the openings of the insulating tubular member. At least one of the cathode and the anode and the insulating tubular member are bonded at a bonded portion with an electrically conductive bonding member; and the bonded portion bonded with the electrically conductive bonding member is coated with a dielectric layer.

30 Claims, 11 Drawing Sheets

(51) Int. Cl.
- *H01J 5/26* (2006.01)
- *G01N 23/02* (2006.01)
- *H01J 9/26* (2006.01)
- *H01J 9/32* (2006.01)
- *H01J 9/36* (2006.01)
- *H01J 9/395* (2006.01)
- *H01J 35/02* (2006.01)
- *H01J 35/20* (2006.01)

(52) U.S. Cl.
CPC .................................. *H01J 9/32* (2013.01); *H01J 9/36* (2013.01); *H01J 9/395* (2013.01); *H01J 35/025* (2013.01); *H01J 35/20* (2013.01); *H01J 2209/18* (2013.01); *H01J 2209/26* (2013.01); *H01J 2235/084* (2013.01)

(56) References Cited

U.S. PATENT DOCUMENTS

| | | | | |
|---|---|---|---|---|
| 6,108,402 A * | 8/2000 | Chornenky | .......... | A61N 5/1001 378/119 |
| 2009/0216317 A1* | 8/2009 | Cromack | ................ | A61L 31/16 514/1.1 |

FOREIGN PATENT DOCUMENTS

| JP | H09-180660 A | 7/1997 |
|---|---|---|
| JP | 2009-021032 A | 1/2009 |
| JP | 2009-245806 A | 10/2009 |

* cited by examiner

RADIATION GENERATING TUBE, RADIATION GENERATING APPARATUS, RADIOGRAPHY SYSTEM AND MANUFACTURING METHOD THEREOF

TECHNICAL FIELD

The present invention relates to a radiation generating tube and a radiation generating apparatus equipped with the same.

BACKGROUND ART

As radiation generating apparatuses have reduced in size and the energy of radiation emitted has increased, enhancing the withstand voltage characteristics (hereinafter referred to as withstand voltage) of radiation generating tubes has been required. One of portions of radiation generating tubes that require withstand voltage is a bonded portion of an insulating tubular member and a cathode. Particularly when the bonded portion is exposed from the radiation generating tube as viewed from the outside thereof, electric field concentration tends to occur in the vicinity of the exposed portion, where discharge is prone to occur. PTL 1 discloses providing a corona ring so as to cover a fusing portion of a glass vacuum envelope and a cathode to relax electric field concentration in the vicinity of the fusing portion, thereby preventing damage to the vacuum envelope due to a local discharge impact.

PTL 2 discloses a structure in which an electrically conducting portion located at the side of a radiation emission window and an electrically insulating portion located at the side of a voltage apply portion are fixed, and an electrically resistive film is disposed outside the electrically insulating portion to prevent discharge due to the disturbance of the electric field between a corona ring and a vacuum envelope.

CITATION LIST

Patent Literature

PTL 1: Japanese Patent Laid-Open No. 07-296754
PTL 2: Japanese Patent Laid-Open No. 2009-245806

SUMMARY OF INVENTION

Technical Problem

Even if the conventional measures for the high withstand voltage are taken, changes in the output intensity of radiation or minute discharge sometimes occur. Such minute discharge causes changes in the current density and the energy of electrons emitted to the target during operation, resulting in changes in radiation output intensity. If the frequency of the minute discharge increases, accelerating voltage cannot be continuously applied between the target and the electron emitting devices.

The present invention provides a radiation generating tube and a radiation generating apparatus having high reliability and high radiation-output stability in which electric field concentration generated at the bonded portion of a cathode or an anode and an insulating tubular member is made difficult to occur, thereby preventing discharge.

Solution to Problem

A radiation generating tube according to an aspect of the present invention includes an envelope including an insulating tubular member having at least two openings, a cathode connected to one of the openings of the insulating tubular member, and an anode connected to the other of the openings of the insulating tubular member; an electron emitting source connected to the cathode; and a target connected to the anode, wherein the internal space of the envelope is under negative pressure relative to the external space, wherein at least one of the cathode and the anode an the insulating tubular member are bonded at a bonded portion with an electrically conductive bonding member; and the bonded portion bonded with the electrically conductive bonding member is coated with a dielectric layer.

Advantageous Effects of Invention

The present invention can provide a high-reliability radiation generating apparatus in which high withstand voltage characteristics are maintained over a long period.

DESCRIPTION OF EMBODIMENTS

An example of the configurations of a radiation generating tube and a radiation generating apparatus according to an embodiment of the present invention will be described with reference to FIG. 1 and FIGS. 2A to 2C.

Figure 1:
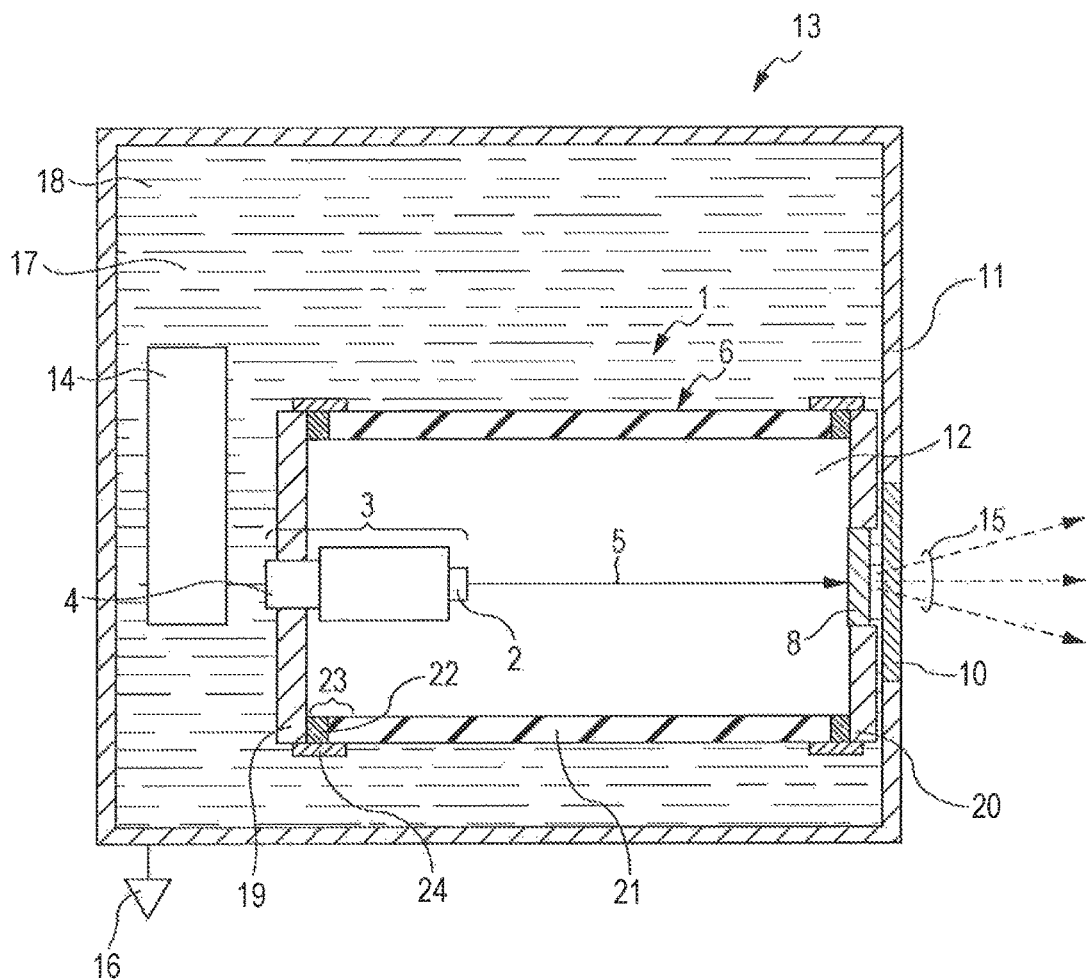
FIG. 1 is a cross-sectional view of a radiation generating apparatus according to an embodiment of the present invention.
Figure 2A:
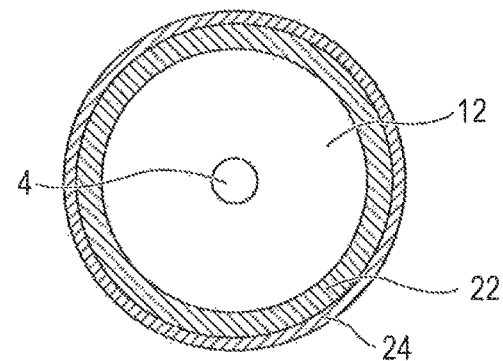
FIG. 2A is a cross-sectional view of a radiation generating tube according to an embodiment of the present invention.
Figure 2B:
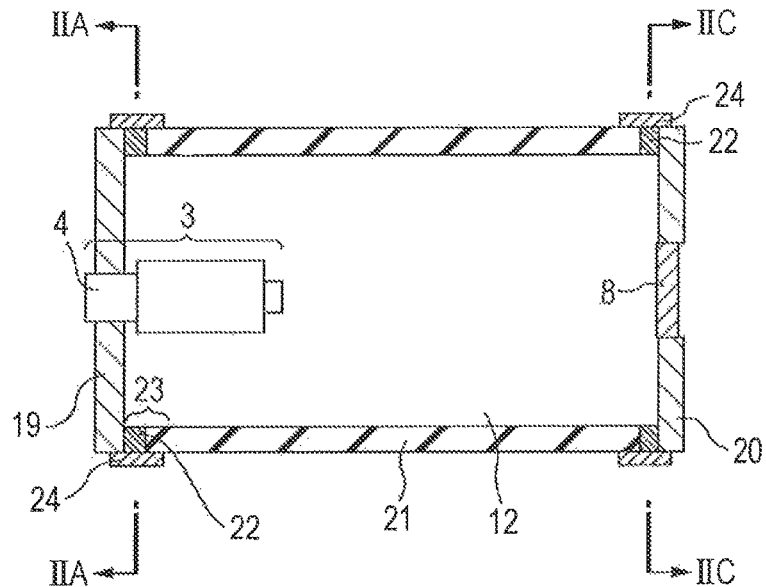
FIG. 2B is a cross-sectional view of the radiation generating tube according to the embodiment of the present invention.
Figure 2C:
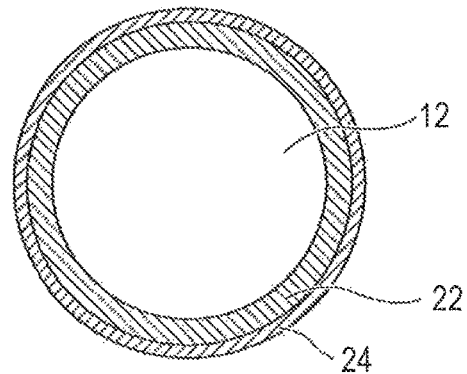
FIG. 2C is a cross-sectional view of the radiation generating tube according to the embodiment of the present invention.
Figure 3:
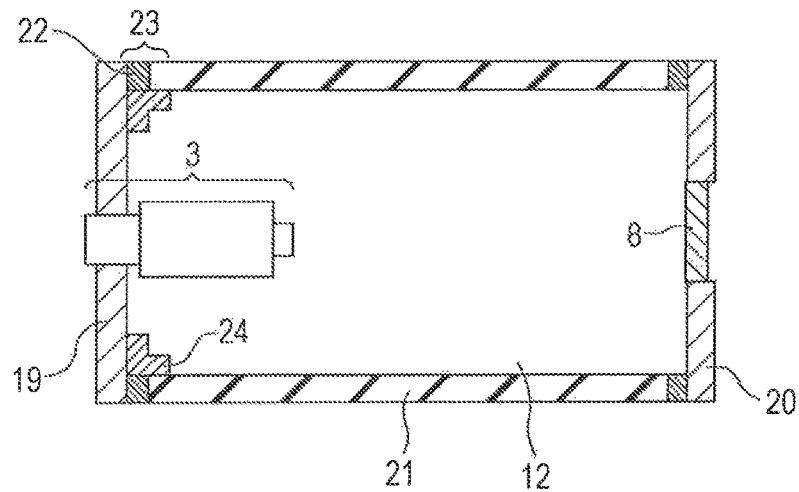
FIG. 3 is a cross-sectional view of a radiation generating tube according to an embodiment of the present invention.

FIGS. 2A to 2C are cross-sectional views of a radiation generating tube according to an embodiment of the present invention, and FIG. 1 is a cross-sectional view of a radiation generating apparatus that accommodates the radiation generating tube according to the embodiment of the present invention.

A radiation generating tube 1 is equipped with a cathode 19, an electron emitting source 3 connected to the cathode 19, an anode 20, a target 8 connected to the anode 20, and an insulating tubular member 21. The cathode 19 and the anode 20 are individually connected to two openings of the insulating tubular member 21 at separate locations. A container 6 formed of the cathode 19, the anode 20, and the insulating tubular member 21 to define an internal space 12 is referred to as an envelope 6 in the present invention. The internal space 12 of the envelope 6 is reduced in pressure (evacuated) so that electrons emitted from an electron emitting portion 2 of the electron emitting source 3 disposed in the internal space 12 of the envelope 6 can be emitted to the target 8 as an electron beam 5. The degree of vacuum in the internal space 12 can be selected as appropriate in consideration of the kind, the driving conditions, and so on of the electron emitting source 3 used; for example, a vacuum level of 1 E-4 to 1 E-8 Pa can be selected. If a cold-cathode electron emitting source of Spindt type, metal-insulator-metal (MIM) type, or the like is used, a vacuum of 1 E-6 Pa or less may be selected in view of the stability of electron emission characteristics. To maintain the degree of vacuum, a getter (not shown) may be disposed in the internal space 12 or an auxiliary space (not shown) that communicates with the internal space 12.

The electron emitting source 3 may be any electron emitting source whose electron emission amount can be controlled from the outside of the envelope 6; for example; in addition to the above-described cold-cathode electron emitting source, a hot-cathode electron emitting source can be applied as appropriate. An impregnated hot-cathode electron emitting source can be employed because it can stably emit a large-current electron beam 5.

The electron emitting source 3 is electrically connected to a driving circuit 14 disposed outside the envelope 6 so that the electron emission amount and the on/off timing of electron emission can be controlled via a current lead-in terminal 4 provided on the cathode 19. The location of the driving circuit 14 is not limited thereto; it may be disposed in the envelope 6.

The cathode 19 according to an embodiment of the present invention defines an electrostatic field around the mounting portion of the electron emitting source 3 to the envelope 6 so as to relax the spatial asymmetry of the electrostatic field around the electron emitting source 3 and to prevent local electric field concentration. The electron emitting source 3 has the electron emitting portion 2. The electron emitting portion 2 has two electrodes that supply emission electron currents as an emitter electrode pair (not shown). If electrooptical functions, such as electron beam convergence and astigmatism correction, are to be added, additional auxiliary electrodes (not, shown) are provided. The electrode group composed of the above-described emitter electrode pair and the auxiliary electrodes can be connected to the driving circuit 14 outside the radiation generating tube 1 from the cathode 19 side via the current lead-in terminal 4. The cathode 19 may be set at a constant potential sufficiently lower than the electrode potential of the anode 20 in view of the relaxation of the asymmetry of the electrostatic field, described above. The potential may be set to the same potential as that of one of the emitter electrode pair that supplies potential to the electron emitting portion 2 or may be set to an intermediate potential of the potentials of the emitter electrode pair.

The anode 20 has functions of defining the potential of the target 8 with a voltage source (not shown) and supplying an anode current flowing in the target 8 to a grounding terminal 16 via the voltage source. The anode 20 is an electrode having the function of defining an electrostatic field around the target 8 of the radiation generating tube 1, like the cathode 19. Accordingly, to prevent local electric field concentration in the electrostatic fields around the electron emitting source 3 and the target 8 and to bring the electric field distribution between the cathode 19 and the anode 20 close to a parallel electric field as much as possible, the cathode 19 and the anode 20 may individually define the potentials of predetermined areas, it may also be the case that the areas are equal to the opening cross-sectional area of the insulating tubular member 21. The anode 20 may separately have a shielding member (not shown) that can define the radiation range of radiation 15. The anode 20 and the target 8 may also be connected via the shielding member.

The materials of the cathode 19 and the anode 20 may be determined depending on electrical conductivity, airtightness, strength, and Coefficient of linear Thermal Expansion matching with the insulating tubular member 21; for example, Kovar and tungsten can be employed.

The target 8 is disposed in the radiation generating tube 1 so as to be irradiated with electrons emitted from the electron emitting portion 2. The target 8 may be opposed to the electron emitting portion 2 in view of the symmetry of the electric field between the cathode 19 and the anode 20.

For the target 8, a positive potential of 10 kV to 200 kV is applied to the electron emitting portion 2, so that electrons having an energy of 10 keV to 200 keV are emitted from the electron emitting portion 2 to the target 8 as the electron beam 5 to cause the target 8 to generate radiation. Accordingly, substantially the same positive potential as that of the target 8 may be applied to anode 20 in view of suppression of asymmetry of the electric field distribution between the cathode 19 and the anode 20. The target 8 has a target component containing a heavy element that generates radiation due to a collision of electrons. The target 8 may be of an independent type composed of only the target component.

An example of the independent type has a configuration in which a diaphragm-type metal thin film is connected to the anode 20. The target 8 may be of a distributed type in which a target material is distributed in a material that allows radiation to pass therethrough and a layered type in which a metal thin film that contains a target material is stacked on a substrate formed of a material that allows radiation to pass there through. Examples of the substrate that allows radiation to pass therethrough include substrates made of a material having a low atomic number, such beryllium and diamond. The target 8 may be of a layered type in which a target layer and a support substrate that supports the target layer are layered. A metal thin film having a thickness of several micrometers may be supported by the substrate in view of prevention of attenuation of radiation and prevention of defocusing due to the thermal deformation of the target 8. The metal thin film may be formed of a heavy metal material having an atomic number 26 or larger in view of radiation/incoming electrons conversion efficiency. Specifically, the metal thin film may be made of tungsten, molybdenum, chrome, copper, cobalt, iron, rhodium, rhenium, or an alloy thereof. If such the metal thin film is formed on the support substrate as a target material of the target 8, any method that ensures the contact between it and the support substrate may be employed; various deposition methods, for example, sputtering, CVD, and vapor deposition, may be employed.

Figure 9A:
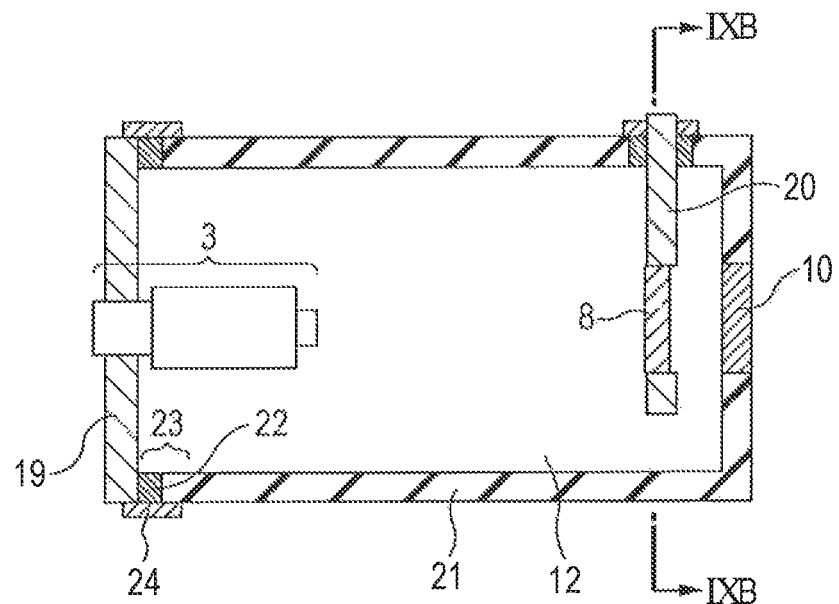
FIG. 9A is a cross-sectional view of a radiation generating tube according to another embodiment of the present invention.
Figure 9B:
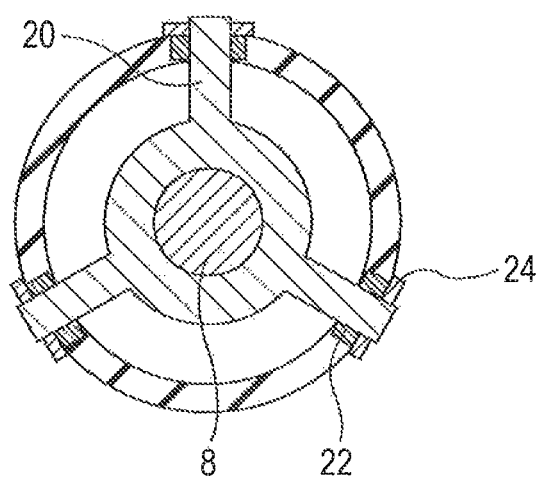
FIG. 9B is a cross-sectional view of the radiation generating tube according to the other embodiment of the present invention.
Figure 9C:
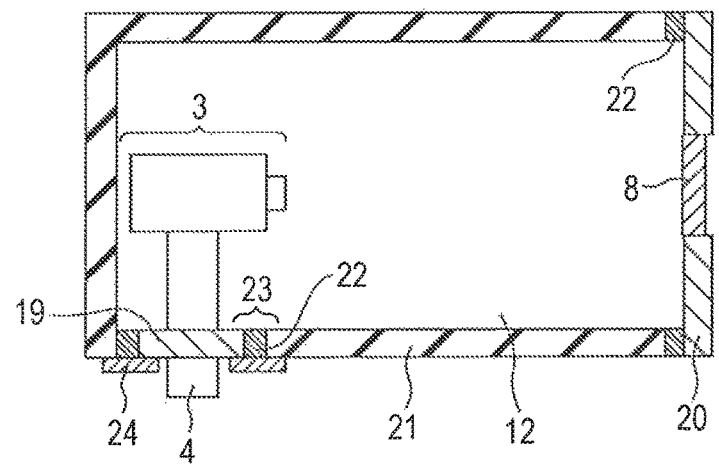
FIG. 9C is a cross-sectional view of a radiation generating tube according to another embodiment of the present invention.
Figure 9D:
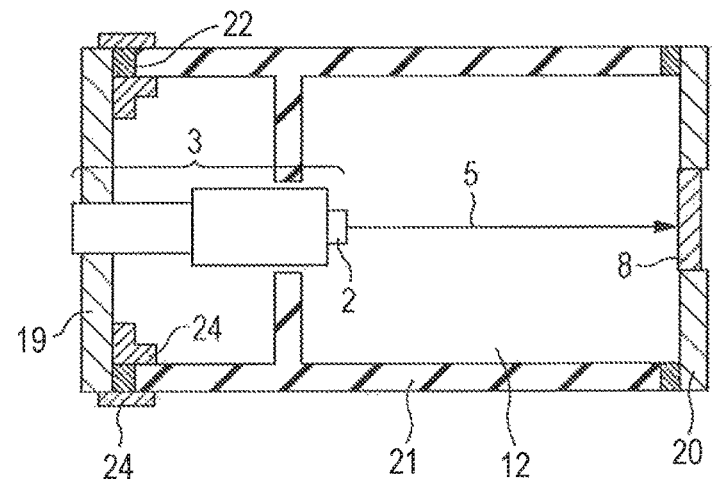
FIG. 9D is a cross-sectional view of a radiation generating tube according to another embodiment of the present invention.

The insulating tubular member 21 has a dielectric property and has at least two openings that connect to the cathode 19 and the anode 20, respectively. The insulating tubular member 21 is configured such that the two openings communicate with each other so that electrons emitted from the electron emitting portion 2 irradiate the target 8 in the envelope 6. That is, the radiation generating tube 1 may have not only the configuration in which the cathode 19 and the anode 20 are exposed and opposed, as shown in FIG. 1, but also a configuration in which the internal space of the insulating tubular member 21 is separated by a partition and the electron emitting source 3 passes through the partition, as shown in FIG. 9D. As shown in FIG. 9A and a cross-sectional view 9B of the radiation generating tube 1 in FIG. 9A, taken along IXB-IXB, the anode 20 (or the cathode 19) may be connected to the side of the insulating tubular member 21. As an alternative, as shown in FIG. 9C, the cathode 19 and the anode 20 need not be opposed and may be in a nonparallel positional relationship. The insulating tubular member 21 need not have a cylindrical shape in cross section, as in FIG. 1, but may have a polygonal outer shape or inner shape in cross section. The material of the insulating tubular member 21 is selected in view of the electrical insulation performance, airtightness, low gas emission performance, heat resistance, and Coefficient of linear Thermal Expansion matching between the cathode 19 and the anode 20; for example, insulating ceramics, such as boron nitride and alumina, and insulating inorganic glass, such as borosilicate glass.

The bonded portion of the cathode 19 or the anode 20 and the insulating tubular member 21 becomes an electric field concentration area when the radiation generating tube 1 is operated, where discharge occurs at high probability, and the withstand voltage characteristics of the radiation generating tube 1 are restricted. Particularly the bonded portion of the cathode 19 and the insulating tubular member 21 is referred to as a triple point, where field electron emission from the cathode 19 side tends to occur. Accordingly, one of measures to reduce discharge is reducing ununiformity of electric field distribution particularly in the vicinity of the bonded portion 23 adjacent to the cathode 19. Disposing the bonded portion 23 via the electrically conductive bonding member 22 as a bonded portion allows the electric field distribution at the triple point to be uniformized around the circumference of the bonded portion 23 (hereinafter referred to as a circumferential direction). the electrically conductive bonding member 22 may be hard solder (brazing alloy), such as silver alloy brazing filler and copper solder, having electrical conductivity and high bondability between different kinds of material, metal and insulator. As shown in FIGS. 2A and 2C, the electrically conductive bonding member 22 may be shaped like a ring and may hermetically seal the bonded portion 23 in a ring shape in view of the uniformity of the electric field in the circumferential direction of the bonded portion 23 of the insulating tubular member 21 and the cathode 19 or the anode 20. FIGS. 2A and 2C are cross-sectional views of the radiation generating tube 1 shown in FIG. 2B, taken along IIA-IIA and IIC-IIC, respectively.

At least one of the cathode 19 and the anode 20 of the radiation generating tube 1 is bonded together with the electrically conductive bonding member 22. The bonded portion 23 having the electrically conductive bonding member 22 interposed therebetween is coated with a dielectric layer 24 made of a dielectric material, such as epoxy resin, silicone resin, aluminum oxide, silicon oxide, and boron nitride.

The dielectric layer 24 exhibits a plurality of actions that improve the withstand voltage characteristics of the radiation generating tube 1 according to an embodiment of the radiation generating tube 1.

The dielectric layer 24 has the action of making the electric field concentration generated at the electrically conductive bonding member 22 difficult to extend directly to the electrostatic field in a space that the electrically conductive bonding member 22 faces. This action will be specifically described hereinbelow.

The electrically conductive bonding member 22 is set to substantially the same potential as that of the cathode 19. Note, however, that the boundary between the electrically conductive bonding member 22 having electrical conductivity, the insulating tubular member 21 having a dielectric property, and the vacuum internal space 12 is a triple point in a microscopic scale, where electric field concentration occurs. On the other hand, in a radiation generating tube manufactured through an actual manufacturing process, sometimes the surface of the electrically conductive bonding member 22 is not formed into a completely smooth surface, and the boundary between the electrically conductive bonding member 22 and the insulating tubular member 21 is not formed into a completely smooth ring shape. For example, the electrically conductive bonding member 22 is a material that comes into close contact with the members which are to be bonded to mutually to ensure a bonded surface in a bonding process, owing to a property of softening to be deformed more easily than the cathode 19 and the insulating tubular member 21 and a property of wettability to members which are to be bonded to mutually. As a result of bonding, local deformation, such as protrusions, and locally spreading wetting occurred in the electrically conductive bonding member 22 to cause the electrically conductive bonding member 22 to be varied in shape. Such variations in the shape of the electrically conductive bonding member 22 further accelerate electric field concentration at the triple point. In the bonded portions 23 shown in FIGS. 10A to 10F, the dielectric layer 24 coats at least the boundary between the electrically conductive bonding member 22 and the insulating tubular member 21. The coating of the bonded portion 23 with the dielectric layer 24 can relax electric field concentration generated at the surface of the electrically conductive bonding member 22 and the boundary between the surface of the electrically conductive bonding member 22 and the insulating tubular member 21. The effect of relaxing the electric field concentration on the space in the vicinity of the bonded portion 23 depends on the relative dielectric constant, the shape, and the coating range of the dielectric layer 24. The relative dielectric constant of the dielectric layer 24 may be smaller than the relative dielectric constant of the insulating tubular member 21. For the configuration of the dielectric layer 24, a thickness of 100 micrometers or more or a thickness of 10% or higher than the thickness of the side wall of the insulating tubular member 21 allows the electric field concentration to be suppressed more effectively. Setting the thickness of the dielectric layer 24 to 100% or less of the thickness of the side wall of the insulating tubular member 21 prevents the electric field concentration area from coming excessively close to the current lead-in terminal 4 or the electrode group of the cathode 19, thus allowing a drop in withstand voltage to be prevented. The coating range of the dielectric layer 24 may be set to at least continuous part of the insulating tubular member 21 next to the boundary between the electrically conductive bonding member 22 and the insulating tubular member 21 in consideration of the alignment tolerance of the coating. The bonded portion 23 including the thickwise direction of the electrically conductive bonding member 22 (the distance between the cathode 19 and the insulating tubular member 21) may be coated. That is, the dielectric layer 24 in FIG. 10C offers a higher field-concentration relaxing effect than that in FIG. 10B, and the dielectric layer 24 in FIG. 10A offers a higher field-concentration relaxing effect than that in FIG. 10C. As shown in FIGS. 10D to 10F, the electrically conductive bonding member 22 and the dielectric layer 24 need not necessarily be in close contact; according to some embodiments of the present invention, there may be a space between the dielectric layer 24 and the electrically conductive bonding member 22. As shown in FIG. 3 and FIGS. 10A to 10D and 10F, a configuration in which one of the side of the electrically conductive bonding member 22 facing the internal space 12 of the envelope 6 and the side of the electrically conductive bonding member 22 facing the external space of the envelope 6 is coated with the dielectric layer 24 is also included as some embodiments of the present invention. Furthermore, as shown in FIG. 10E, a configuration in which both of the surface of the electrically conductive bonding member 22 facing the internal space 12 of the envelope 6 and the surface of the electrically conductive bonding member 22 facing the external space of the envelope 6 are coated so as to sandwich the electrically conductive bonding member 22 therebetween is also included as an embodiment of the present invention. As shown in FIGS. 2A and 2C, the dielectric layer 24 may be shaped like a ring and may coat the bonded portion 23 in a ring shape in view of the uniformity of the electric field in the circumferential direction of the bonded portion 23.

As described above, the dielectric layer 24 has the operational advantage of directly suppressing electric field concentration in the vicinity of the bonded portion 23. Furthermore, as shown in FIGS. 10A, 10D, 10E, and 10F, the dielectric layer 24 has the operational advantage of indirectly suppressing electric field concentration in the vicinity of the bonded portion 23, depending on the configuration of coating. This will be described hereinbelow.

The target 8 generates the radiation 15 when irradiated with the electron beam 5. The conversion efficiency thereof is extremely smaller than 1. Most of the kinetic energy of the electron beam 5 input to the target 8 is converted to heat and does not contribute to generation of radiation. Accordingly, the bonded portion 23 of the radiation generating tube 1 is subjected to a temperature change history from a storage temperature (environmental temperature or room temperature) in an inoperative state to an operating temperature (the order of several hundred Celsius degrees). Furthermore, continuous compressive stress occurs in the bonded portion 23 due to the pressure difference (atmospheric pressure) between the interior and the exterior of the radiation generating tube 1. Furthermore, in the radiation generating tube 1, a linear expansion amount difference due to a Coefficient of linear Thermal Expansion difference between the cathode 19 or the anode 20 and the insulating tubular member 21 and the temperature distribution occurs among the components due to the temperature changes, described above. The mismatch of the Coefficient of linear Thermal Expansion and the liner expansion amount causes an intermittent and changing stress in the bonded portion 23.

Figure 7A:
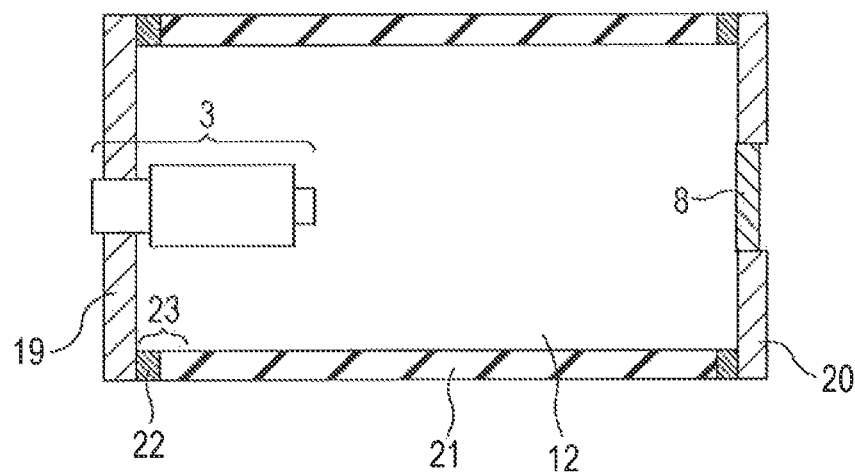
FIG. 7A is a schematic diagram for explaining an action of the present invention.
Figure 7B:
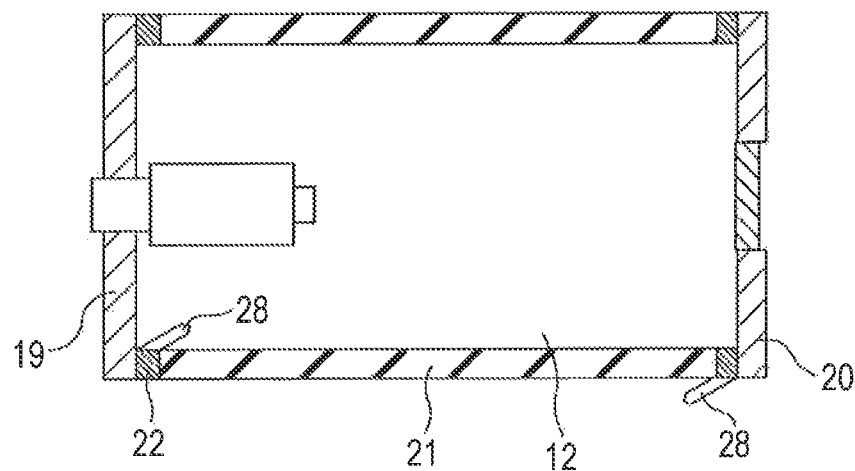
FIG. 7B is a schematic diagram for explaining an action of the present invention.

As mentioned above, there are some probabilities of cracks due to the stresses within the radiation generating tube. One of the stresses concerned with the linear expansion difference due to the operating temperature changes and the other of the stresses concerned with the pressure difference between the interior and exterior of the radiation generating tube. The bonded portion 23 with the electrically conductive bonding member 22 that contains metal, such as silver alloy brazing filler, has a faculty to prevent cracks, breaking, and so on in the other components of the radiation generating tube 1 due to distortion (deformation) of the electrically conductive bonding member 22, such as viscoelastic deformation. However, the stress that is generated in the bonded portion 23 for a long period, described above, and the repletion thereof serve as driving force to grow needle crystal 28 called whisker from the electrically conductive bonding member 22. Specifically, the electrically conductive bonding member 22 is an alloy made of hard solder, such as silver alloy brazing filler, and has the property of relaxing compressive stress generated in the alloy when subjected to continuous stress, particularly, compressive stress by generating needle crystal 28 of a selected component thereof, such as silver, copper, gold, zinc, and tin, outwards from the surface of the alloy composition. The inventors have found that the withstand voltage characteristics sometimes deteriorate due to the needle crystal 28 protruding from the surface of the electrically conductive bonding member 22. FIG. 7A shows the initial state of the radiation generating tube 1 in which the bonded portions 23 of the insulating tubular member 21 and the cathode 19 and the anode 20 are not coated with dielectric layers. FIG. 7B schematically shows the same radiation generating tube 1 after being operated for 1,000 hours. Since the needle crystal 28 has electrical conductivity and has a shape with a high aspect ratio (length in a growing direction/cross-sectional width), it caused further acceleration of the electric field concentration in the vicinity of the bonded portion 23.

The dielectric layer 24 has the action of physically preventing the needle crystal 28 from protruding from the surface of the electrically conductive bonding member 22 into a space in the vicinity of the bonded portion 23 by covering the bonded portion 23. Accordingly, the coating of the bonded portion 23 with the dielectric layer 24 is effective particularly when the electrically conductive bonding member 22 contains a metal element selected from silver, tin, zinc, and gold as simple metal, or metal elements selected therefrom as components of an alloy or components of a metal mixture.

Figure 10A:
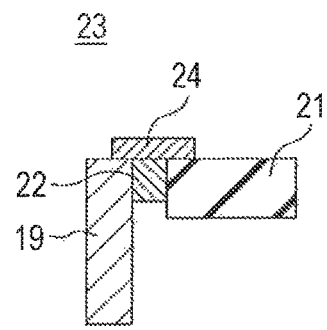
FIG. 10A is a cross-sectional view showing the state of coating of the bonded portion of the dielectric layer of a radiation generating tube according to an embodiment of the present invention.
Figure 10B:
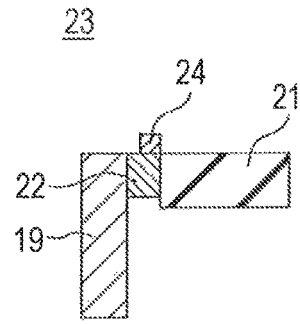
FIG. 10B is a cross-sectional view showing the state of coating of the bonded portion of the dielectric layer of a radiation generating tube according to an embodiment of the present invention.
Figure 10C:
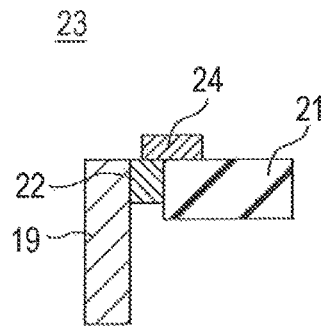
FIG. 10C is a cross-sectional view showing the state of coating of the bonded portion of the dielectric layer of a radiation generating tube according to an embodiment of the present invention.
Figure 10D:
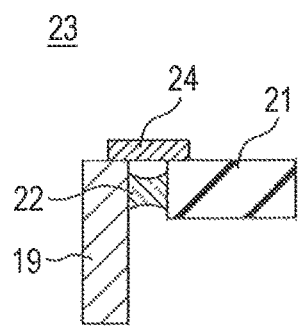
FIG. 10D is a cross-sectional view showing the state of coating of the bonded portion of the dielectric layer of a radiation generating tube according to an embodiment of the present invention.
Figure 10E:
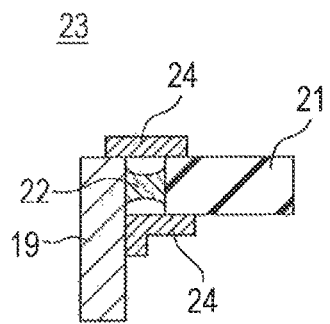
FIG. 10E is a cross-sectional view showing the state of coating of the bonded portion of the dielectric layer of a radiation generating tube according to an embodiment of the present invention.
Figure 10F:
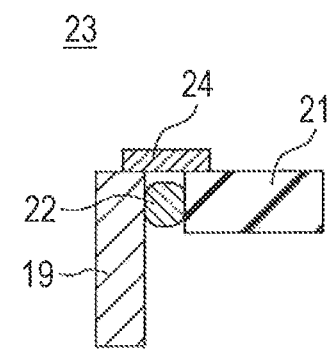
FIG. 10F is a cross-sectional view showing the state of coating of the bonded portion of the dielectric layer of a radiation generating tube according to an embodiment of the present invention.

Furthermore, as shown in FIGS. 10A, 10D, and 10F, the dielectric layer 24 may be configured to coat both of part of the cathode 19 and part of the insulating tubular member 21 in such a manner so as to connect the cathode 19 and the insulating tubular member 21. In other words, the dielectric layer 24 may be configured to coat part of the members which are to be bonded to mutually to be bonded by the bonded portion 23 in such a manner as to bridge the members which are to be bonded to mutually. Such a configuration allows part of the stress generated in the electrically conductive bonding member 23 to be shared by the dielectric layer 24 to reduce the stress generated in the electrically conductive bonding member 22, thereby preventing generation of the needle crystal 28. Furthermore, as shown in FIG. 10E, providing both of a configuration in which both of the side of the electrically conductive bonding member 22 facing the internal space 12 of the envelope 6 and the side of the electrically conductive bonding member 22 facing the external space of the envelope 6 are coated, with the electrically conductive bonding member 22 interposed therebetween, and the configuration in which the cathode 19 and the insulating tubular member 21, which are target members, are coated so as to be bridged allows the action of sharing part of the stress generated in the bonded portion 23, described above, to be further enhanced. Although FIGS. 10A to 10F illustrate the bonded portion 23 at the cathode 19 side, the bonded portion 23 at the anode 20 side offers the same operational advantages as those of the bonded portion 23 at the cathode 19 side by employing the same configurations as those of the bonded portion 23 at the cathode 19 side.

Furthermore, the process of manufacturing the radiation generating apparatus 1 includes the step of bonding at least one of the cathode 19 and the anode 20 and an opening of the insulating tubular member 21 with the electrically conductive bonding member 22; the step of coating the bonded portion 23 with the dielectric layer 24 so as to bridge part of at least one of the cathode 19 and the anode 20 and part of the insulating tubular member 21; the step of forming the envelope 6 by defining the internal space 12 by hermetically sealing the cathode 19, the anode 20, and the insulating tubular member 21; and the step of reducing the pressure of the internal space 12 of the envelope 6 into negative pressure relative to an external space. By performing the pressure-reducing step after the step of coating the bonded portion 23 with the dielectric layer 24, compressive stress generated in the bonded portion 23 due to the negative pressure in the internal space of the envelope 6 can be reduced more effectively by forming the dielectric layer 24 before compressive stress is generated in the bonded portion 23, particularly in the electrically conductive bonding member 22.

Figure 8A:
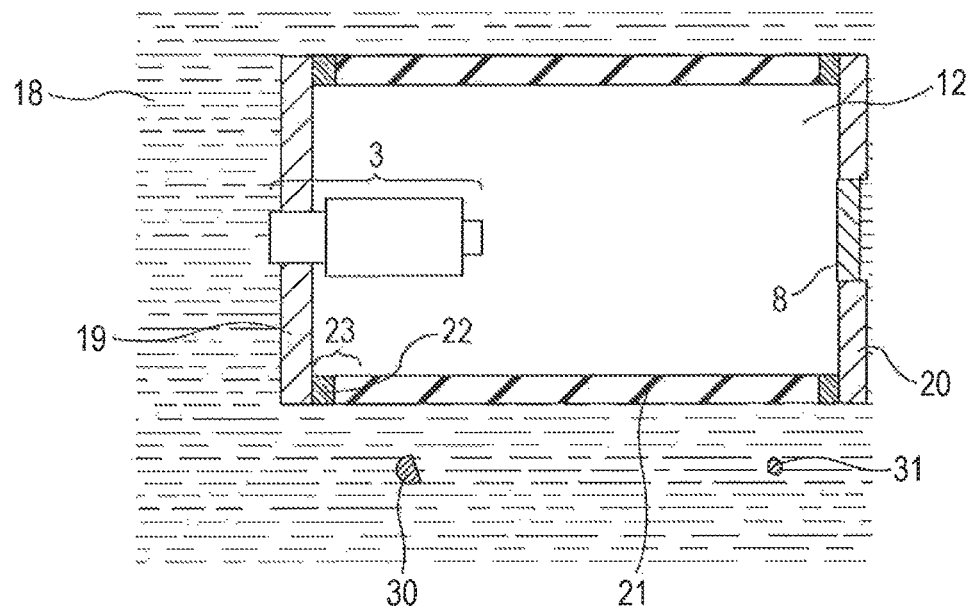
FIG. 8A is a schematic diagram for explaining another action of the present invention.

The radiation generating tube 1 may be accommodated in the container 11 to configure the radiation generating apparatus 13. The internal space 17 between the radiation generating tube 1 and the container 11 may accommodate insulating fluid (insulating liquid 18) in view of stabilization of the withstand voltage characteristics and the performance characteristics of the radiation generating apparatus 13 in operation. The introduction of the insulating liquid 18 can enhance the heat radiation performance of the radiation generating tube 1 in operation while ensuring the insulation between the cathode 19 and the anode 20. The insulating liquid 18 may have high electrical insulation performance, high cooling performance and is less prone to degradation due to heat; for example, electrically insulating oil, such as silicone oil, transformer oil, and fluorine oil and fluorine insulating liquid, such as hydrofluoroether, can be used. However, in the case where the insulating liquid 18 is disposed around the radiation generating tube 1, sometime a foreign substance 31 gets mixed or a foreign substance 30 is generated in the insulating liquid 18, as shown in FIG. 8A. Possible causes of the contaminant foreign substance 31 are dropping-off of part of some of the components that constitute the radiation generating apparatus 13 resulting from deterioration due to heat generated during operation or vibration during operation and inevitable intrusion thereof into the insulating liquid 18 during manufacture. Possible causes of the generated foreign substance 30 are deterioration of the insulating liquid 18 itself into a solid due to an increase in the temperature of the insulating liquid 18, absorption of electromagnetic waves, or the like with the operation of the radiation generating apparatus (hereinafter the contaminant foreign substance 31 and the generated foreign substance 30 are collectively referred to as foreign substances).

Figure 8B:
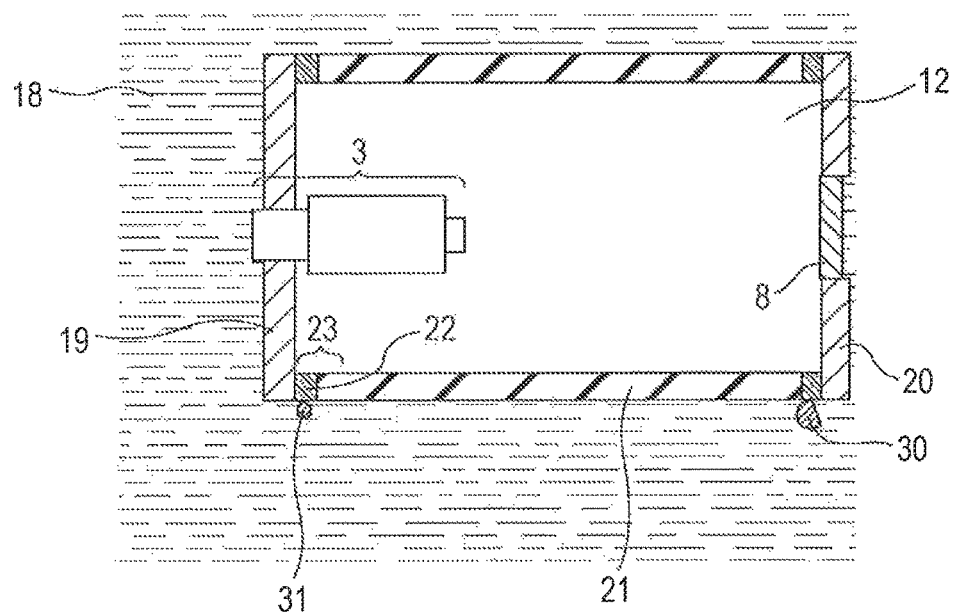
FIG. 8B is a schematic diagram for explaining the other action of the present invention.

As shown in FIG. 8B, these foreign substances sometimes come into contact with the bonded portion 23 of the cathode 19 or anode 20 and the insulating tubular member 21 as the insulating liquid 18 flows. The contact between the bonded portion 23 and the foreign substances, irrespective of whether the foreign substances have electrical conductivity or dielectricity, has a possibility that the electric field distribution in the vicinity of the bonded portion 23 is locally disturbed to cause a new electric field concentration area.

The dielectric layer 24 also has the effect of suppressing the generation of an electric field concentration area due to the contact between the foreign substances in the insulating liquid 18 and the bonded portion 23 by obstructing such contact itself between the foreign substances and the bonded portion 23 in the insulating liquid 18. Accordingly, as shown in FIG. 1, at least part of the outer surface 6 of the insulating tubular member 21 and the electrically conductive bonding member 22 are continuously coated so as to separate the insulating liquid 18 and the bonded portion 23 from each other using the dielectric layer 24.

Furthermore, by setting the relative dielectric constant of the insulating liquid 18 smaller than that of the dielectric layer 24, the electric field concentration in the vicinity of the bonded portion 23 can be further relaxed.

The driving circuit 14 for driving the radiation generating tube 1 may be disposed either inside or outside the container 11.

The container 11 may be set at a predetermined potential in view of operational stability and safety of the radiation generating apparatus 13. The predetermined potential may be a grounding potential set via the grounding terminal 16. The material of the container 11 may be various kinds of material; for example, metal, such as iron, stainless steel, lead, brass, and copper, may be employed in view of radiation shielding performance, strength, and surface-potential setting performance.

The auxiliary electrode may be connected to a collection circuit (not shown) disposed outside the radiation generating tube 1. Both of the correction circuit and the voltage source may be provided in the driving circuit 14.

EXAMPLES

Example 1

Figure 4:
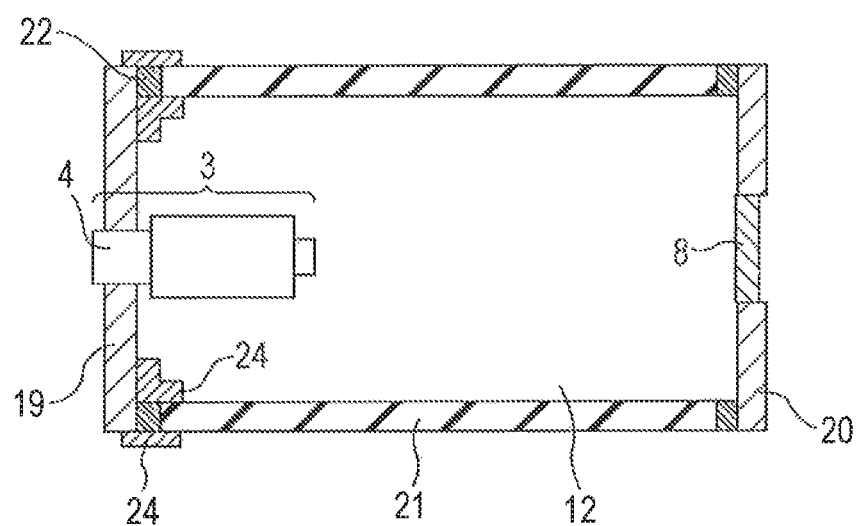
FIG. 4 is a cross-sectional view of a radiation generating tube according to an embodiment of the present invention.
Figure 5:
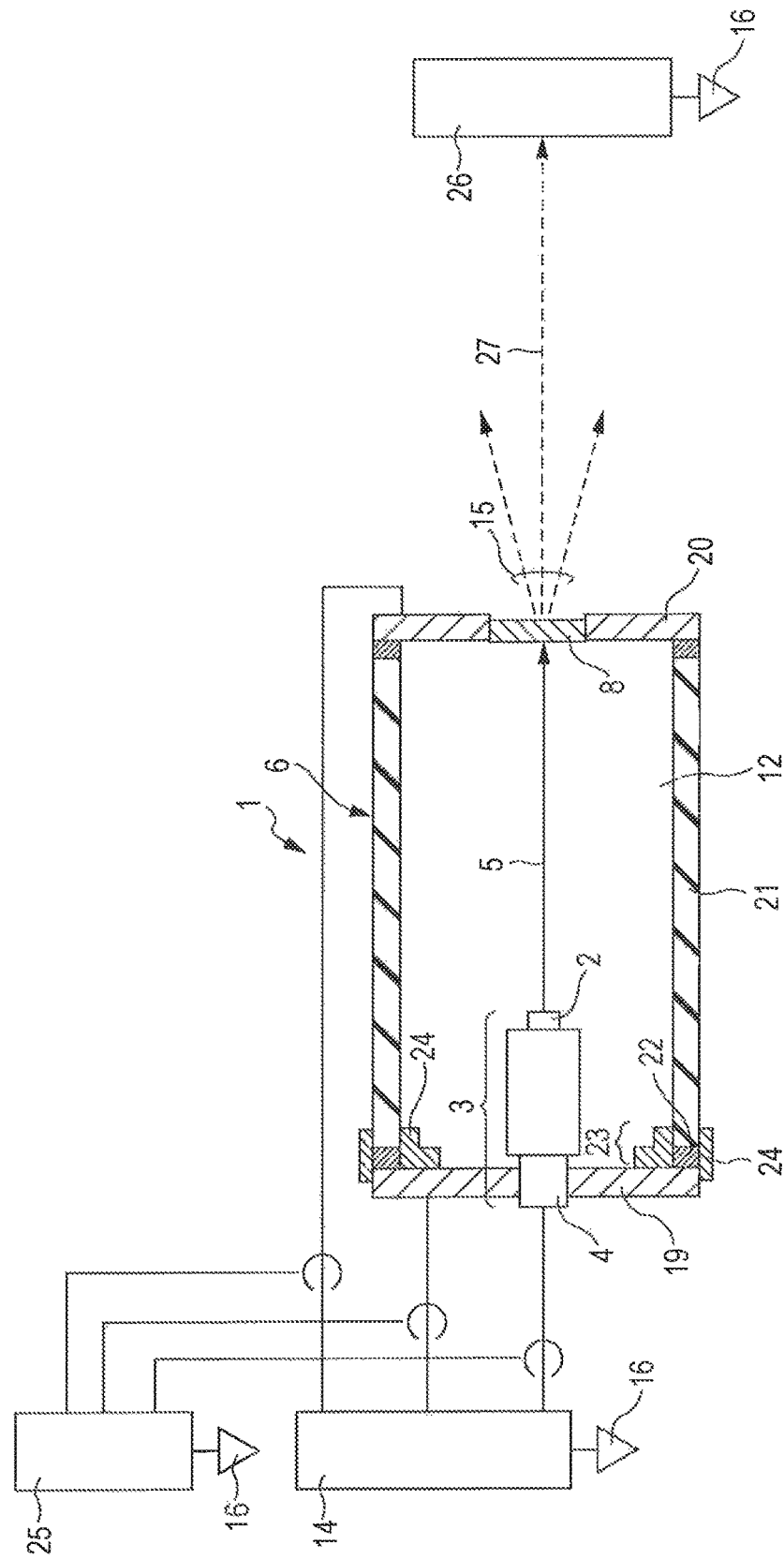
FIG. 5 is a block diagram of an experimental device according to an embodiment of the present invention.

Example 1 is an example of the configuration shown in the foregoing embodiment and will be described in detail using FIGS. 4 and 5. FIG. 4 shows a cross-section of the radiation generating tube 1 of Example 1. FIG. 5 is a block diagram of an experimental device for examining the performance characteristics of the radiation generating tube 1 of Example 1.

The radiation generating tube 1 of Example 1 was formed as follows. First, a high-pressure synthetic diamond made by Sumitomo electric industries, Ltd., was prepared as a support substrate. The support substrate has a disc shape (cylindrical shape) having a diameter of 5 mm and a thickness of 1 mm. The prepared support substrate was subjected to UV-ozone ashing to remove organic matter on the surface thereof.

A titanium contact layer was formed by sputtering at a thickness of 10 nm on one of the two circular surfaces of the support substrate having a diameter of 1 mm by using argon as a carrier gas. The support substrate during deposition of titanium was heated to 260 Celsius degrees with a heating stage. Next, a tungsten target layer was formed by sputtering at a thickness of 7 micrometers on the contact layer by continuous deposition using argon as a carrier gas without venting an atmosphere around the deposition unit. The diamond support substrate during deposition of tungsten was heated to 260 Celsius degrees with a heating stage, as in the deposition of titanium.

The thicknesses of the titanium contact layer and the tungsten target layer were adjusted to designated film thicknesses depending on the deposition times before the deposition by acquiring calibration curve data about the thicknesses of the individual films and deposition times in advance. Measurement of the film thicknesses for acquiring the calibration curve data was performed using a spectroscopic ellipsometer, UVISEL ER, made by Horiba, Ltd. Thus, the target 8 in which the diamond support substrate, the titanium contact layer, and the tungsten target layer were deposited in this order was obtained.

Next, a cylindrical opening having a diameter of 1.1 mm was formed in the center of a disc-shaped metal plate formed of Kovar and having a diameter of 60 mm and a thickness of 3 mm to form the anode 20. The anode 20 was subjected to organic solvent cleaning, rinse, and UV-ozone ashing to remove organic matter on the surface of the anode 20.

Next, silver alloy brazing filler was applied between the opening of the anode 20 and the outer circumference of the disc-shaped target 8 as an electrically conductive bonding member to solder them, and thus the anode 20 connected to the target 8 was obtained.

Next, the current lead-in terminal 4 was provided at the center of a disc-shaped metal plate made of Kovar and having a diameter of 60 mm and a thickness of 3 mm to form the cathode 19. The cathode 19 was subjected to cleaning similar to that for the anode 20, such as organic solvent cleaning, rinse, and UV-ozone ashing, to remove organic matter on the surface of the cathode 19.

Next, the current lead-in terminal 4 and an impregnated electron gun were electrically and mechanically connected to obtain the cathode 19 connected to the electron emitting source 3.

Next, the insulating tubular member 21 made of alumina and having a length of 70 mm, an outside diameter of 60 mm, and an inside diameter of 50 mm was prepared. The insulating tubular member 21 was also subjected to cleaning similar to that for the cathode 19 and the anode 20 to remove organic matter on the surface thereof.

Next, ring-shaped silver alloy brazing filler, Japanese Industrial Standard, BAg-8 (Ag72-Cu28, melting point: 780 Celsius degrees), was inserted between the surface of the cathode 19 on which the electron emitting source 3 is provided and one of the openings of the insulating tubular member 21 and is subjected to brazing at 820 Celsius degrees to form the bonded portion 23 having the ring-shaped hermetically bonded bonding member 22. Thus, the insulating tubular member 21 bonded to the cathode 19 was obtained.

Next, as shown in FIG. 4, a two-component epoxy adhesive is applied to the side of the bonded portion 23 of the cathode 19 and the insulating tubular member 21 exposed to the interior of the insulating tubular member 21 and the side of the bonded portion 23 exposed to the outside of the insulating tubular member 21 and is hardened. Thus, the bonded portion 23 is coated with the dielectric layers 24 formed of epoxy resin obtained by hardening the epoxy adhesive so as to sandwich the bonded portion 23 therebetween. The coating ranges of the dielectric layers 24 were set to a range of 1 mm from the boundary between the cathode 19 and the electrically conductive bonding member 22 toward the cathode 19 to 5 mm from the boundary between the insulating tubular member 21 and the electrically conductive bonding member 22 toward the anode 20 on both of inside and outside of the insulating tubular member 21. The thickness of the dielectric layers 24 used was set to 1 mm. The relative dielectric constant of the alumina in the insulating tubular member 21 was 9.5 (at room temperature, 1 MHz). The relative dielectric constant of the epoxy resin used was 4.0 (at room temperature, 1 MHz). The melting point of the alumina in the insulating tubular member 21 was 2,020 Celsius degrees.

Next, the other of the openings of the insulating tubular member 21 and the same exposed surface of the anode 20 as the surface of the target 8 from which tungsten is exposed was soldered by inserting ring-shaped silver alloy brazing filler, Japanese Industrial Standard, BAg-8 (Ag72-Cu28, melting point: 780 Celsius degrees), in the same manner as the bonding of the cathode 19 side to form the bonded portion 23 having the ring-shaped hermetically bonded bonding member 22.

Thus, the cathode 19 and the anode 20 and the insulating tubular member 21 are individually connected at the two openings of the insulating tubular member 21 by airtight bonding to form the envelope 6.

Next, the interior of the envelope 6 was evacuated to a vacuum of 1E-5 Pa with an exhaust pipe and an exhauster (not shown), and thereafter the exhaust pipe is sealed to form the radiation generating tube 1.

Five radiation generating tubes 1, shown in FIG. 4, were formed by the method described above.

As shown in FIG. 5, the formed radiation generating tubes 1 were disposed in the atmosphere, and the cathode 19, the anode 20, and the current lead-in terminal 4 of each of the radiation generating tubes 1 were connected to a cathode terminal that outputs $-\frac{1}{2}$ Va, an anode terminal that outputs $+\frac{1}{2}$ Va, and a terminal group that controls the amount of electrons of the electron beam 5 to be emitted from the electron gun 3, which are provided in the driving circuit 14 in advance, where Va is an acceleration voltage between the electron emitting portion 2 and the target 8.

Next, a radiation-intensity detector 26 equipped with a semiconductor detector was disposed at a position 100 cm away from the target 8 on the central vertical axis of the target 8 of the radiation generating apparatus 1, that is, a position on the radiation emission center axis. Output-stability evaluation with the radiation-intensity detector 26 was performed in such a manner that radiation was emitted for five seconds every time the electron emitting source 3 repeats 100 times of a one-second emission and a three-second idle period, with the acceleration voltage Va set at 60 kV, the output intensity of radiation was measured for three seconds except the preceding and following one seconds, and thus, temporal changes in the output intensity of the radiation generating tube 1 were measured. The electron emission was performed in such a manner that the emission axis of the electron beam 5 was aligned so that the focus on the target 8 is well within the target 8, and the spot radius of the electron beam 5 is 0.5 mm, and the density of a current flowing in the anode 20 was controlled to a variable value within 1% while monitoring the current flowing through the path between the anode 20 and the grounding electrode with a negative feedback circuit (not shown).

The discharge counter 25 observed whether discharge has occurred in a connection wire from the cathode 19 to the driving circuit 14, a connection wire from the anode 20 to the driving circuit 14, and a connection wire group from the current lead-in terminal 4 to the driving circuit 14 with inductive probes. A discharge-withstand-voltage characteristic test was performed by gradually increasing the acceleration voltage Va while stopping the current supplied to the electron emitting portion 2.

The average value of the output changes of the radiation generating tubes 1 of Example 1 was 1.9%, which was a good result.

Furthermore, the average of voltages that the radiation generating tubes 1 of Example 1 discharged first was 91 kV, and the average of the accumulated numbers of discharge to an application of 100 kV was 1.3, which were good results.

As shown in FIG. 5, in the foregoing experiment, the discharge counter 25, the driving circuit 14, and the radiation-intensity detector 26 were grounded with the grounding terminal 16.

Another five radiation generating tubes 1 of Example 1 were formed, and when the individual bonded portions 23 were observed by conducting a test to give a 1,000-hour temperature history in which temperatures from a room temperature to 300 Celsius degrees are repeated 100 times using environment testing equipment, as in Example 1, no needle crystal was observed at the cathode-side bonded portions 23 and the anode-side bonded portions 23.

Comparative Example 1

The process of forming the radiation generating tubes 1 was performed as in Example 1, except the step of coating with the dielectric layers 24, to form five radiation generating tubes 1 shown in FIG. 7A.

A radiation-intensity-output-stability test and a discharge-withstand-voltage characteristic test were performed on the radiation generating tubes 1 formed in Comparative Example 1 for the experimental device shown in FIG. 5, as in Example 1.

The average value of the output changes of the radiation generating tubes 1 of Comparative Example 1 was 3.9%, the performance of which was poorer than that of Example 1.

Furthermore, the average of voltages that the radiation generating tubes 1 of Comparative Example 1 discharged first was 65 kV, and the average of the accumulated numbers of discharge to an application of 100 kV was 12.3, the performance of which was poorer than that of Example 1.

Another five radiation generating tubes 1 of Comparative Example 1 were formed, and when the individual bonded portions 23 were Observed by conducting a test to give a 1,000-hour temperature history in which temperatures from a room temperature to 300 Celsius degrees are repeated 100 times using environment testing equipment, as in Example 1, three pieces of needle crystal 28 were observed at two locations on the cathode 19 side and one location on the anode 20 side.

Example 2

In the step of forming the dielectric layers 24 on the cathode-side bonded portion 23 of the process of forming the radiation generating tubes 1 in Example 1, the dielectric layer 24 was formed only on the inside of the insulating tubular member 21, and the other forming steps were performed as in Example 1 to form five radiation generating tubes 1 shown in FIG. 7A.

A radiation-intensity-output-stability test and a discharge-withstand-voltage characteristic test were performed on the radiation generating tubes 1 formed in Example 2 for the experimental device shown in FIG. 5, as in Example 1.

The average value of the output changes of the radiation generating tubes 1 of Example 2 was 2.3%, which was a good result.

Furthermore, the average of voltages that the radiation generating tubes 1 of Example 2 discharged first was 84 kV, and the average of the accumulated numbers of discharge to an application of 100 kV was 1.6, which was a good result.

Another five radiation generating tubes 1 of Example 2 were formed, and when the individual bonded portions 23 were observed by conducting a test to give a 1,000-hour temperature history in which temperatures from a room temperature to 300 Celsius degrees are repeated 100 times using environment testing equipment, as in Example 1, no needle crystal was observed at the cathode-side bonded portions 23 and the anode-side bonded portions 23.

Example 3

Figure 6:
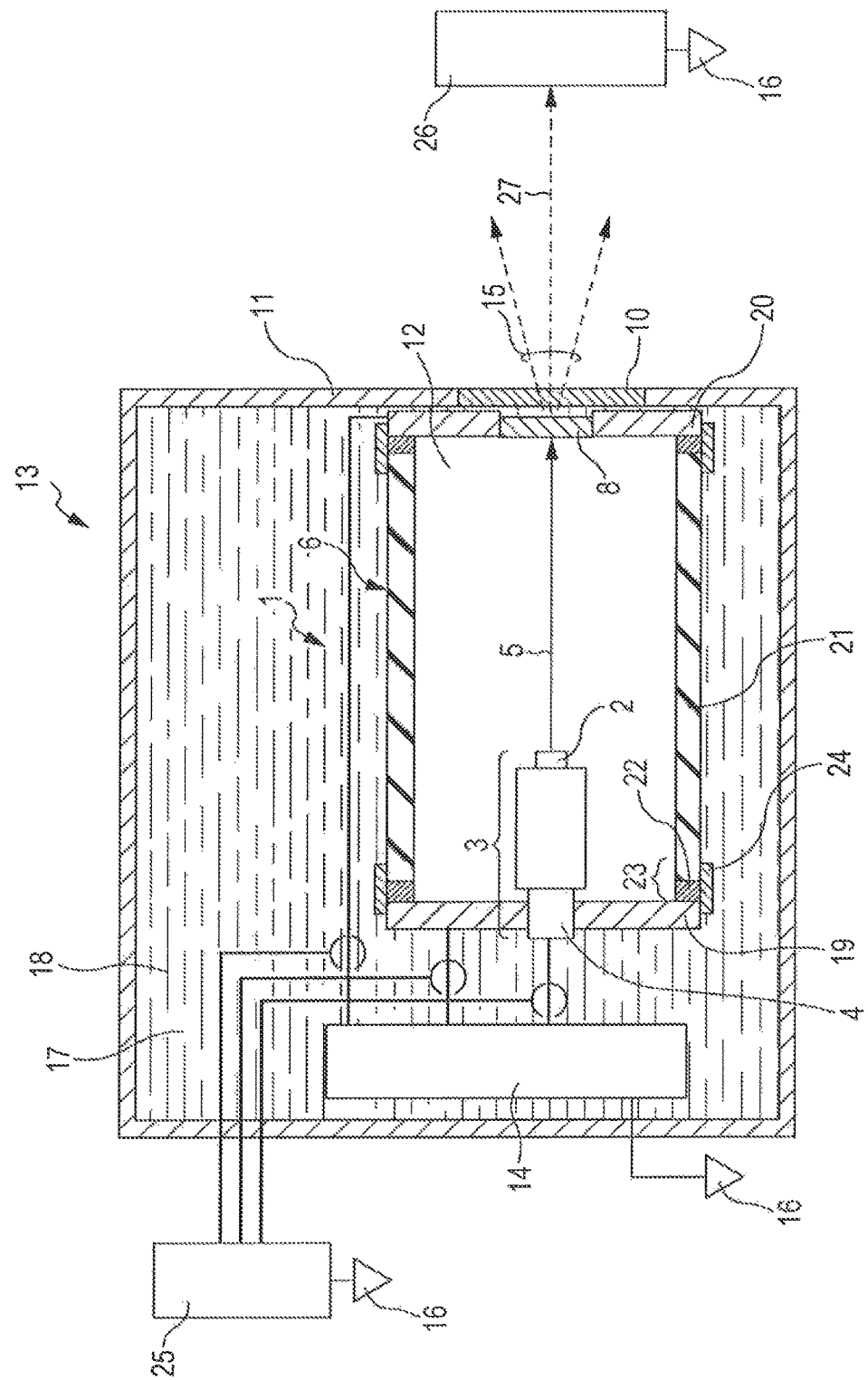
FIG. 6 is a block diagram of an experimental device according to an embodiment of the present invention.

In Example 3, in the step of forming the dielectric layers 24 on the bonded portion 23 of the same forming method as in Example 1, the dielectric layer 24 was formed only on the outside of the envelope 6 as in Example 1, except that both of bonded portion 23 at the cathode 19 side and the bonded portion 23 at the anode 20 side were coated with dielectric layers 24, to form five radiation generating tubes 1 shown in FIGS. 2A, 2B, and 2C. Next, as shown in FIG. 6, the thus-formed radiation generating tubes 1 were each accommodated in the brass container 11 together with the driving circuit 14. Next, as in Example 1, the driving circuit 14 and the radiation generating tube 1 were electrically connected. Next, as in Example 1, the dielectric probes of the discharge counter 25 disposed outside the container 11 were disposed on connection wires between the driving circuit 14 and the radiation generating tube 1, and the container 11 was filled with silicone oil having a relative dielectric constant of 2.8 (at room temperature, 1 MHz), and thereafter, the container 11 was closed with a brass cover. Thus, the radiation generating apparatus 13 whose output changes can be measured was formed.

Next, for the thus-formed radiation generating apparatus 13, the radiation-intensity detector 26 equipped with the semiconductor detector was disposed at a position facing a radiation extracting portion 10 of the container 11, on the radiation irradiation center axis 27, and 100 cm distant from the target 8, as in Example 1.

The average value of the output changes of the radiation generating tubes 3 of Example 3 was 2.0%, which was a good result.

Furthermore, the average of voltages that the radiation generating tubes 1 of this example discharged first was 94 kV, and the average of the accumulated numbers of discharge to an application of 100 kV was 1.3, which was a good result.

When the five radiation generating apparatuses 13 of Example 3 subjected to the output-stability estimation test were disassembled, and the bonded portions 23 of the individual radiation generating tubes 1 were observed, 3.3 foreign substances were observed on the dielectric layer 24 at the cathode 19 side, and 7.2 foreign substances were observed on the dielectric layer 24 at the anode side on average, Comparative Example 2

The process of forming the radiation generating tubes 1 in Example 3 was performed as in Example 1, except the step of coating with the dielectric layers 24, to form five radiation generating tubes 21 shown in FIG. 7A. The thus-formed radiation generating apparatuses 13 were each accommodated in the container 11, as in Example 3, and were filled with the insulating liquid 18 formed of silicone oil, and the radiation generating tube 5 was connected to the driving circuit 14, the discharge counter 25, and the radiation-intensity detector 26.

A radiation-intensity-output-stability test and a discharge-withstand-voltage characteristic test were performed on the radiation generating tubes 1 formed in Comparative Example 2 for the experimental device shown in FIG. 6, as in Example 3.

The average value of the output changes of the radiation generating tubes 1 of Comparative Example 2 was 3.8%, the performance of which was poorer than that in Example 3.

Furthermore, the average of voltages that the radiation generating tubes 1 of Comparative Example 2 discharged first was 62 kV, and the average of the accumulated numbers of discharge to an application of 100 kV was 11.1, the performance of which was poorer than that of Example 3.

When the five radiation generating apparatuses 13 subjected to the output-stability estimation test of Comparative Example 2 were disassembled, and the bonded portions 23 of the individual radiation generating tubes 1 were observed, 3.2 foreign substances were observed on the bonded portion 23 at the cathode 19 side, and 7.6 foreign substances were observed on the bonded portion 23 at the anode side on average.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-245793, filed Nov. 9, 2011, which is hereby incorporated by reference herein in its entirety.

The invention claimed is:

1. A radiation generating tube comprising:
an envelope including an insulating tube having a pair of openings, a cathode connected to one of the pair of openings of the insulating tube, and an anode connected to the other of the pair of openings of the insulating tube;
an electron emitting source connected to the cathode; and
a target connected to the anode,
wherein the insulating tube and at least any one of the cathode and the anode are bonded via a conductive bonding member so as to form a triple junction at a boundary between the insulating tube, the conductive bonding member, and vacuum inside the envelope; and
wherein the boundary is coated with a dielectric layer without at least any of the one of the cathode and the anode intervened therebetween so as to relax electric field concentration due to the triple junction.

2. The radiation generating tube according to claim 1, wherein the dielectric layer coats at least part of the conductive bonding member and at least part of the insulating tube next to the conductive bonding member.

3. The radiation generating tube according to claim 1, wherein the dielectric layer coats at least part of an outer surface of the insulating tube.

4. The radiation generating tube according to claim 1, wherein the dielectric layer coats the bonded portion so as to bridge.

5. The radiation generating tube according to claim 1, wherein the dielectric layer has a relative dielectric constant smaller than a relative dielectric constant of the insulating tube.

6. The radiation generating tube according to claim 1, wherein the dielectric layer contains at least one dielectric material selected from epoxy resin, silicone resin, silicon oxide, aluminum oxide, and boron nitride.

7. The radiation generating tube according to claim 1, wherein the dielectric layer has a thickness of 10% or more and 100% or less of a thickness of a wall of the envelope located at the bonded portion.

8. The radiation generating tube according to claim 7, wherein the conductive material bonding member is silver alloy brazing filler.

9. The radiation generating tube according to claim 1, wherein the conductive bonding member contains metal elements selected from silver, tin, zinc, and gold as components of an alloy.

10. The radiation generating tube according to claim 1, wherein the conductive bonding member is shaped a ring and hermetically bonds the bonded portion in a ring shape.

11. The radiation generating tube according to claim 1, wherein the dielectric layer is shaped a ring and coats the bonded portion in a ring shape.

12. A radiation generating apparatus comprising:
the radiation generating tube according to claim 1;
a container that accommodates the radiation generating tube; and
insulating liquid in a space between the container and the radiation generating tube.

13. The radiation generating apparatus according to claim 12, wherein the insulating liquid has a relative dielectric constant smaller than a relative dielectric constant of the dielectric layer.

14. The radiation generating apparatus according to claim 12, wherein the insulating liquid is at least any one of silicone oil, transformer oil, or fluorine oil.

15. A radiography system comprising:
the radiation generating apparatus according to claim 12; and
a radiation detector that detects radiation that is radiated from the radiation generating apparatus and is transmitted through a subject.

16. The radiation generating tube according to claim 1, wherein an internal space surrounded by the cathode, the anode and the insulating tube is under negative pressure relative to an external space.

17. The radiation generating tube according to claim 16, wherein the dielectric layer coats a side of the conductive bonding member facing the internal space of the envelope and the side of the conductive bonding member facing the external space of the envelope so as to sandwich the conductive material bonding member therebetween.

18. A radiation generating tube comprising:
an envelope including an insulating tube having a pair of openings, a cathode connected to one of the pair of openings of the insulating tube, and an anode connected to the other of the pair of openings of the insulating tube;
an electron emitting source connected to the cathode; and
a target connected to the anode,
wherein the insulating tube and at least any one of the cathode and the anode are bonded via a conductive bonding member so as to form a proximal electrical end which is the closest end in the conductive bonding member in a distance to the other of the cathode and the anode, and
wherein the proximal electrical end is coated with a dielectric layer so as to relax electric field concentration occurring at the proximal electrical end.

19. The radiation generating tube according to claim 18, wherein the dielectric layer coats at least part of the conductive bonding member and at least part of the insulating tube next to the conductive bonding member.

20. The radiation generating tube according to claim 18, wherein the dielectric layer coats at least part of an outer surface of the insulating tube.

21. The radiation generating tube according to claim 18, wherein the dielectric layer coats the bonded portion so as to bridge.

22. The radiation generating tube according to claim 18, wherein an internal space surrounded by the cathode, the anode and the insulating tube is under negative pressure relative to an external space.

23. The radiation generating tube according to claim 22, wherein the dielectric layer coats a side of the conductive bonding member facing the internal space of the envelope and the side of the conductive bonding member facing the external space of the envelope so as to sandwich the conductive material bonding member therebetween.

24. The radiation generating tube according to claim 18, wherein the dielectric layer has a relative dielectric constant smaller than a relative dielectric constant of the insulating tube.

25. The radiation generating tube according to claim 18, wherein the dielectric layer contains at least one dielectric material selected from epoxy resin, silicone resin, silicon oxide, aluminum oxide, and boron nitride.

26. The radiation generating tube according to claim 18, wherein the dielectric layer has a thickness of 10% or more and 100% or less of a thickness of a wall of the envelope located at the bonded portion.

27. The radiation generating tube according to claim 26, wherein the conductive material bonding member is silver alloy brazing filler.

28. The radiation generating tube according to claim 18, wherein the conductive bonding member contains metal elements selected from silver, tin, zinc, and gold as components of an alloy.

29. The radiation generating tube according to claim 18, wherein the conductive bonding member is shaped a ring and hermetically bonds the bonded portion in a ring shape.

30. The radiation generating tube according to claim 18, wherein the dielectric layer is shaped a ring and coats the bonded portion in a ring shape.

* * * * *